US012685443B2

(12) United States Patent
Pawar et al.

(10) Patent No.: US 12,685,443 B2
(45) Date of Patent: Jul. 21, 2026

(54) METHOD AND SYSTEM FOR MONITORING HUMAN PARAMETERS USING HIERARCHIAL HUMAN ACTIVITY SENSING

(71) Applicant: Tata Consultancy Services Limited, Mumbai (IN)

(72) Inventors: Bhaskar Ramchandra Pawar, Thane (IN); Sakyajit Bhattacharya, Kolkata (IN); Karan Rajesh Bhavsar, Thane (IN); Avik Ghose, Kolkata (IN); Varsha Sharma, Indore (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 199 days.

(21) Appl. No.: 18/752,973

(22) Filed: Jun. 25, 2024

(65) Prior Publication Data

US 2025/0031966 A1     Jan. 30, 2025

(30) Foreign Application Priority Data

Jul. 24, 2023     (IN) .............................. 202321049900

(51) Int. Cl.
| | |
|---|---|
| *A61B 5/00* | (2006.01) |
| *G16Y 20/20* | (2020.01) |
| *G16Y 40/10* | (2020.01) |

(52) U.S. Cl.
CPC ............ *A61B 5/0024* (2013.01); *G16Y 20/20* (2020.01); *G16Y 40/10* (2020.01)

(58) Field of Classification Search
CPC ... A61B 5/0024; A61B 5/7267; A61B 5/0022; A61B 5/7264; G16Y 20/20; G16Y 40/10; G16H 40/67; G16H 50/20; H04L 67/12
See application file for complete search history.

(56) References Cited

U.S. PATENT DOCUMENTS 11,178,010 B2     11/2021   Kozhaya et al.

OTHER PUBLICATIONS

Farzad Samie et al., "Hierarchical Classification for Constrained IoT Devices: A Case Study on Human Activity Recognition," EEE Internet of Things, Apr. 2020, IEEE, https://www.researchgate.net/publication/340720316_Hierarchical_Classification_for_Constrained_IoT_Devices_A_Case_Study_on_Human_Activity_Recognition.

(Continued)

*Primary Examiner* — Joel Lamprecht
(74) *Attorney, Agent, or Firm* — FINNEGAN, HENDERSON, FARABOW, GARRETT & DUNNER LLP

(57)     ABSTRACT

This disclosure relates generally to method and system for monitoring human parameters using hierarchical human activity sensing. The method is based on sensing as service (SEAS) model which processes continuous mobility data from multiple sensors on the client edge-device by optimizing the on-device processing pipelines. The method requests a subject to select a human parameter of the human body to be monitored using a master device and capture the plurality of signals by recognizing sensors corresponding to the health parameter. The master device transmits to the server the subject selected human parameter of the human body to be monitored and requesting the server to recommend a hierarchical classifier structure. Further, the human body is monitored based on the on-device hierarchical sensing pipeline by executing a plurality of algorithms. In addition, the system is suitable for remote monitoring and flexible edge cloud arbitration, optimizing costs, infrastructure, and energy.

20 Claims, 13 Drawing Sheets

(56) References Cited

OTHER PUBLICATIONS

Marcin Straczkiewicz et al., A systematic review of smartphone-based human activity recognition methods for health research, NPJ Digital Medicine, 2021, Nature, https://www.nature.com/articles/s41746-021-00514-4.

Hui Liu et al., "A Practical Wearable Sensor-Based Human Activity Recognition Research Pipeline," EEE Internet of Things, 2022, https://www.researchgate.net/publication/358567885_A_Practical_Wearable_Sensor-Based_Human_Activity_Recognition_Research_Pipeline.

200

202          204          222

Algorithm Library          Algorithm Instances

Algorithm Factory  206

Master Mode

OnDevice SeaS Agent

HAR  Classifier Service          Parameter of Interest Evaluator

Slave Mode 208          210

Raw Data Preprocessor          AlgorithmService Pairing Agent          Device Capability Evaluator 212          214          216

Device API Abstraction Layer  218

IoT Device 220          sensory devices 224

① Activity tracking using Standalone Wrist-Wearable Device

② Activity tracking using Wrist-Wearable Device Tethered With Smart Phone

③ Activity tracking using Smart-Wearable-Belt Device Tethered With Smart Phone

④ Activity tracking using only Smart Phone

300 pre-processing by initiating a service launch application on at least one of (i) an IoT device among a plurality of IoT devices and (ii) a sensory device among a plurality of sensory devices attached to a human body, identifying a master device from the plurality of IoT devices and the plurality of sensory devices and a communication is established between the master device and a server, and transmitting by the master device a plurality of sensors configurations of each IoT device and each sensory device to a server

302 requesting a subject to select a human parameter of the human body to be monitored using the master device and capturing the plurality of signals by recognizing sensors corresponding to the health parameter

304 transmitting by the master device to the server the subject selected human parameter of the human body to be monitored and requesting the server to recommend a hierarchical classifier structure corresponding to at least one health parameter of interest corresponding to the human parameter for the plurality of sensor configurations of the master device

306 receiving by the master device from the server an on-device hierarchical sensing pipeline suitable for at least one health parameter of interest corresponding to the human parameter and processing the on-device hierarchical sensing pipeline on the master device

308 monitoring by the master device the human parameter of the human body based on the on-device hierarchical sensing pipeline by executing a plurality of algorithms on the master device corresponding to the human parameter, wherein the plurality of algorithms corresponds to at least one parameter of interest of the human parameter

310 extracting a plurality of features from the plurality of signals being captured by the plurality of the sensors and classifying the plurality of features corresponding to the human parameter using a XG boost classifier model

Figure 7A:
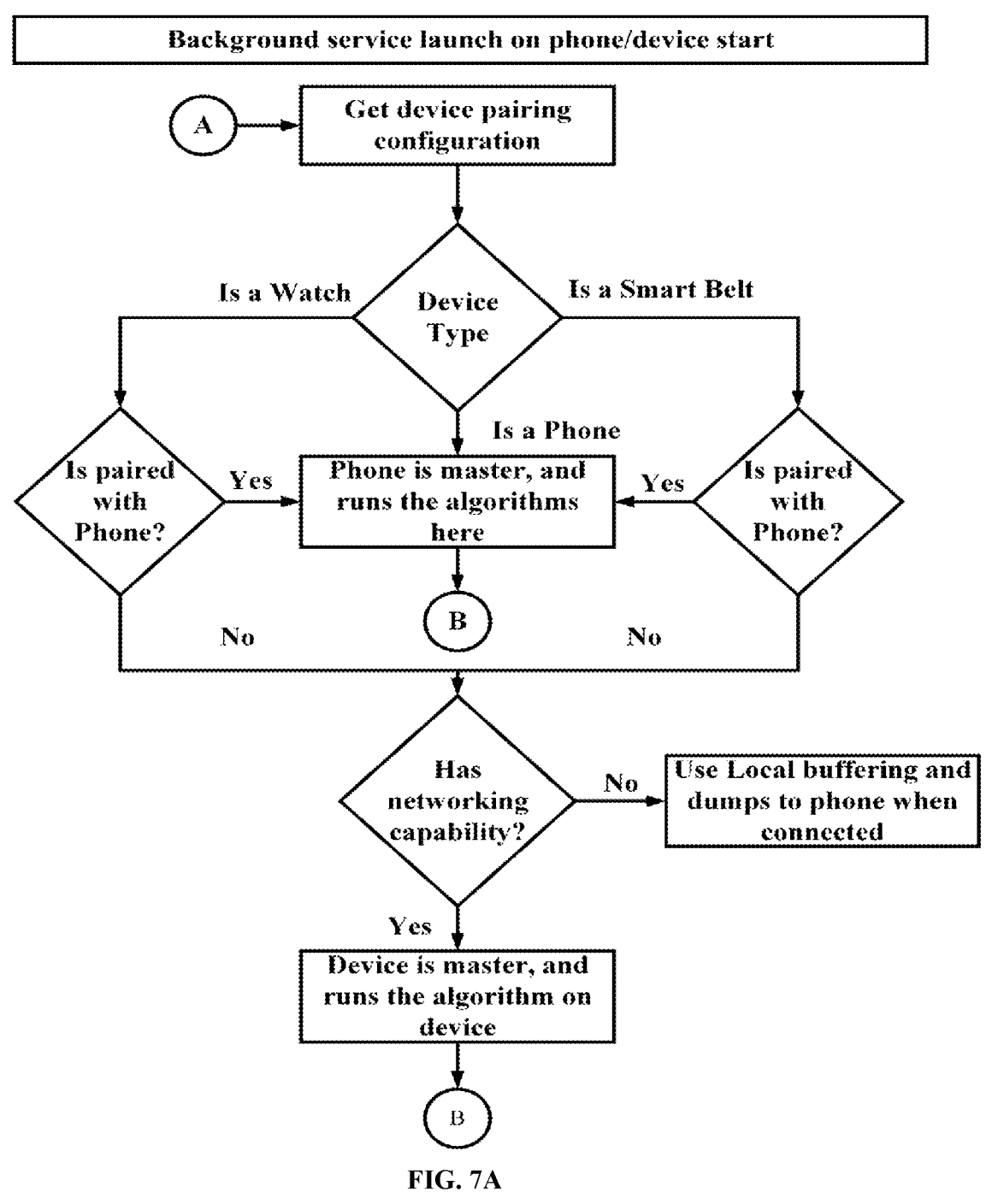

Background service launch on phone/device start

(A) → Get device pairing configuration

Device Type

Is a Watch

Is a Smart Belt

Is a Phone

Is paired with Phone? — Yes → Phone is master, and runs the algorithms here ← Yes — Is paired with Phone?

No     (B)     No

Has networking capability? — No → Use Local buffering and dumps to phone when connected

Yes

Device is master, and runs the algorithm on device

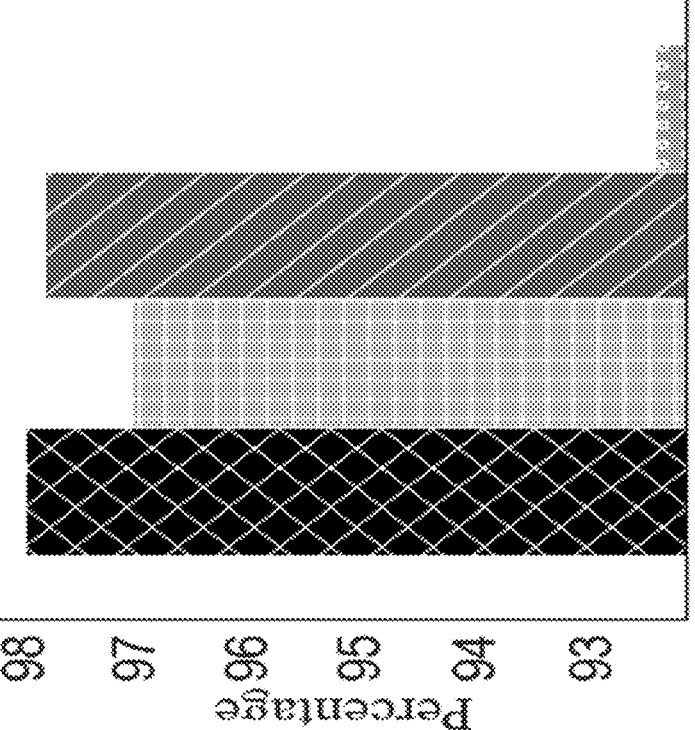
FIG. 8B

METHOD AND SYSTEM FOR MONITORING HUMAN PARAMETERS USING HIERARCHIAL HUMAN ACTIVITY SENSING

PRIORITY CLAIM

This U.S. patent application claims priority under 35 U.S.C. § 119 to: Indian Patent Application number 202321049900, filed on 24th July 2023. The entire contents of the aforementioned application are incorporated herein by reference.

TECHNICAL FIELD

The disclosure herein generally relates to monitoring human parameters activities of daily living (ADLs), and, more particularly, to method and system for monitoring human parameters using hierarchical human activity sensing.

BACKGROUND

Human Activity Recognition (HAR) has been playing an increasingly important role in almost all aspects of HAR application such as wearable devices, sensors, machine learning, and deep learning for human activity recognition (HAR) applications has increased in recent years. Activity detection using sensors embedded in smart and wearable devices offers a great opportunity to understand and detect human behavior in holistic view of an individual's health and well-being. Numerous computational techniques have been applied to sensor streams to detect daily living activities. However, most methods fail to capture different levels of activity hidden in human behavior. Also, the performance of the model decreases as the number of activities increases.

Functional monitoring of a human state of health, physical and mental performance, or recovery from injury, hospitalization, or treatment is a subject of most medicine, such as geriatrics, rehabilitation and physical therapy, neurology and orthopedics, and nursing are most important HAR application. Continuous monitoring and analysis of human activity is crucial and essential to support a healthy and active lifestyle. This can be achieved in care centers and nursing homes without time limits by using various types of sensor devices. On-body IMU sensors, radar-based sensors such as ultra-wideband (UWB), camera-based sensors, and more. Different types of sensors produce different types of raw data and may require appropriate preprocessing pipelines depending on the application, case. Some use cases require sensors to be "always on", thus generating large amounts of data. In such scenarios, existing techniques consume memory, storage and are not scalable. Such large amount of data should preferably be processed optimally over edge or cloud to reduce data transfer, storage, and resource costs. Existing techniques lack in determining which area of the human body to be currently focused for monitoring and analysis when the subject has on-body sensors all the time and processing responsibility. Further, the existing techniques lack in processing data when these sensors do not have access to nearby edge server or cloud server via internet.

SUMMARY

Embodiments of the present disclosure present technological improvements as solutions to one or more of the above-mentioned technical problems recognized by the inventors in conventional systems. For example, in one embodiment, a system for monitoring human parameters using hierarchical human activity sensing is provided. The system includes pre-processing by initiating a service launch application on at least one of an IoT device among a plurality of IoT devices and a sensory device among a plurality of sensory devices attached to a human body, wherein each of the sensory device and each of the IoT device captures a plurality of signals via a plurality of sensors. Further, a master device is identified from the plurality of IoT devices and the plurality of sensory devices and a communication is established between the master device and a server, and the master device transmits a plurality of sensors configurations of each IoT device and each sensory device to a server.

Further a subject selects a human parameter of the human body to be monitored using the master device and capturing the plurality of signals recognizing sensors corresponding to the health parameter, wherein the master device transmits the plurality of signals corresponding to the health parameter of the human body to the server. The master device transmits to the server the subject selected human parameter of the human body to be monitored and requesting the server to recommend a hierarchical classifier structure corresponding to at least one health parameter of interest corresponding to the human parameter for the plurality of sensor configurations of the master device.

The master device receives from the server an on-device hierarchical sensing pipeline suitable for at least one health parameter of interest corresponding to the human parameter and processing the on-device hierarchical sensing pipeline on the master device. The master device monitors the human parameter of the human body based on the on-device hierarchical sensing pipeline by executing a plurality of algorithms on the master device corresponding to the human parameter, wherein the plurality of algorithms corresponds to at least one parameter of interest of the human parameter.

In another aspect, a method for monitoring human parameters using hierarchical human activity sensing is provided. The method includes pre-processing by initiating a service launch application on at least one of an IoT device among a plurality of IoT devices and a sensory device among a plurality of sensory devices attached to a human body, wherein each of the sensory device and each of the IoT device captures a plurality of signals via a plurality of sensors. Further, a master device is identified from the plurality of IoT devices, and the plurality of sensory devices and a communication is established between the master device and a server, and the master device transmits a plurality of sensors configurations of each IoT device and each sensory device to a server.

Further a subject selects a human parameter of the human body to be monitored using the master device and capturing the plurality of signals recognizing sensors corresponding to the health parameter, wherein the master device transmits the plurality of signals corresponding to the health parameter of the human body to the server. The master device transmits to the server the subject selected human parameter of the human body to be monitored and requesting the server to recommend a hierarchical classifier structure corresponding to at least one health parameter of interest corresponding to the human parameter for the plurality of sensor configurations of the master device.

The master device receives from the server an on-device hierarchical sensing pipeline suitable for at least one health parameter of interest corresponding to the human parameter and processing the on-device hierarchical sensing pipeline on the master device. The master device monitors the human parameter of the human body based on the on-device hierarchical sensing pipeline by executing a plurality of algorithms on the master device corresponding to the human parameter, wherein the plurality of algorithms corresponds to at least one parameter of interest of the human parameter.

In yet another aspect, there are provided one or more non-transitory machine-readable information storage mediums comprising one or more instructions, which when executed by one or more hardware processors causes a method for monitoring human parameters using hierarchical human activity sensing.

The method initially pre-processes by initiating a service launch application on at least one of an IoT device among a plurality of IoT devices and a sensory device among a plurality of sensory devices attached to a human body, wherein each of the sensory device and each of the IoT device captures a plurality of signals via a plurality of sensors. Further, a master device is identified from the plurality of IoT devices, and the plurality of sensory devices and a communication is established between the master device and a server, and the master device transmits a plurality of sensors configurations of each IoT device and each sensory device to a server.

Further a subject selects a human parameter of the human body to be monitored using the master device and capturing the plurality of signals recognizing sensors corresponding to the health parameter, wherein the master device transmits the plurality of signals corresponding to the health parameter of the human body to the server. The master device transmits to the server the subject selected human parameter of the human body to be monitored and requesting the server to recommend a hierarchical classifier structure corresponding to at least one health parameter of interest corresponding to the human parameter for the plurality of sensor configurations of the master device.

The master device receives from the server an on-device hierarchical sensing pipeline suitable for at least one health parameter of interest corresponding to the human parameter and processing the on-device hierarchical sensing pipeline on the master device. The master device monitors the human parameter of the human body based on the on-device hierarchical sensing pipeline by executing a plurality of algorithms on the master device corresponding to the human parameter, wherein the plurality of algorithms corresponds to at least one parameter of interest of the human parameter.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles:

FIG. 3 is a flowchart of an exemplary method of operation for monitoring human parameters using the system of FIG. 1, in accordance with some embodiments of the present disclosure.

FIG. 7A and FIG. 7B illustrates an example method of operation for monitoring human parameters using the system of FIG. 1 corresponding to the plurality of sensors in accordance with some embodiments of the present disclosure.

FIG. 8B illustrates a graphical representation of comparison of existing techniques with the present disclosure using the system of FIG. 1 in accordance with some embodiments of the present disclosure.

DETAILED DESCRIPTION

Figure 1:
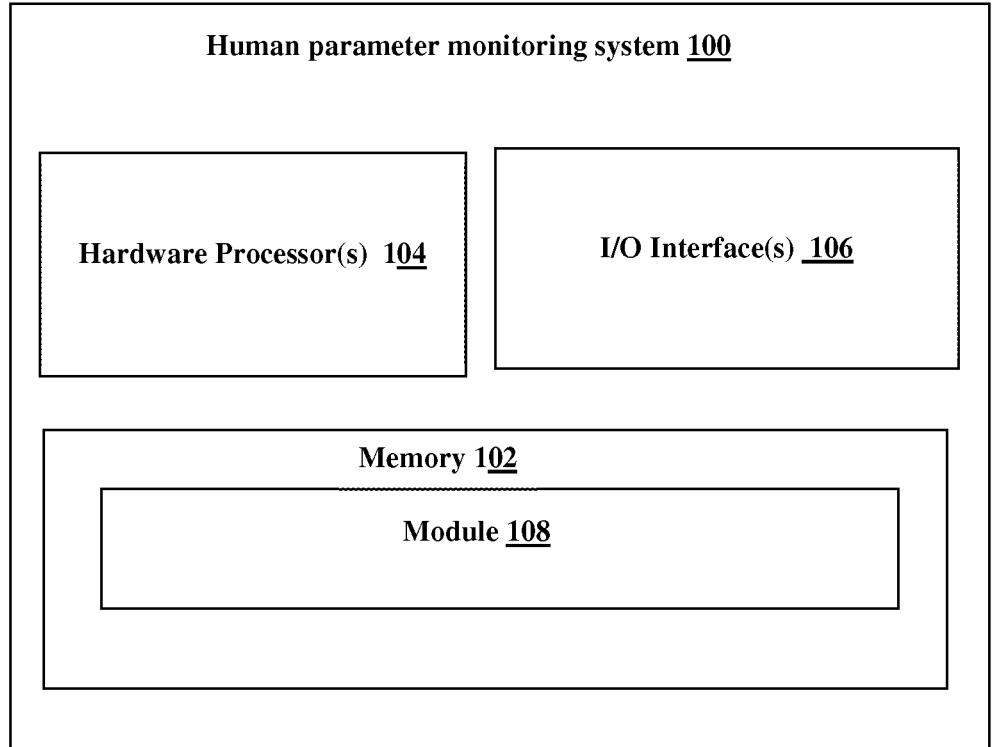
FIG. 1 is an illustrative system (alternatively referred as human parameter monitoring system) to monitor human health, in accordance with some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Human activities, specifically activities of daily living (ADL) reveal vastly about a subject behavior, frame of mind, endurance abnormalities while performing certain activities. Detection of daily human activities is a key component in modern applications of Internet of Things. There are many different methods to detect the activity of an individual where several types of sensors are used. Recent technological advances in smartphones (and other handheld, "smart" devices) and even their increasing daily use by the general public, has transformed mobile sensing into a very interesting research area. The increased computational capabilities, the large sets of embedded sensors and the mobile nature of smartphones give to new potentials but also include new challenges.

In conventional approaches, recognition of human activities via a set of sensors are coupled to a device for monitoring specific human parameters for example wearable devices, smartwatch, and the like. However, sensing devices are fixed at predetermined points of interest, so the inference of activities entirely depends on the voluntary interaction of the subjects with the sensors while the devices for internal sensing are attached to the subject, which leads to wearable based human activity recognition (HAR). However, the HAR considers various factors such as hardware (equipment, sensor design, sensing technology, among others), software (acquisition, data visualization, signal processing, among others), and machine learning (ML) approaches (feature study, modeling, training, recognition, evaluation, among others) for activities being performed by the subject. In such scenarios computing large amount of data on devices are crucial and time consuming.

Embodiments herein provide a method and system for monitoring human parameters using hierarchical human activity sensing. The system may be alternatively referred as a human parameter monitoring system. The system focus on providing activity detection and monitoring problem using sensing capabilities of devices for monitoring human parameters based on Sensing as Service (SEAS) model. In order to recognize daily human activities, the sensor data for example an accelerometer and the like need to be suitably processed. Then, for each detection process (motion, environment, and activity) the features are extracted from the aforementioned procedure and classified using a machine learning model. The recognition models are created for each machine learning algorithm for classification of activities of daily living (ADL). Finally, the layer models are combined in a hierarchical sensing approach to achieve an accurate activity monitoring. The method of the present disclosure processes continuous mobility data from a plurality of sensors on client edge-device by optimizing on-device hierarchical sensing processing pipelines. Thus, cost of data transfer and CPU usage is reduced. The disclosed system is further explained with the method as described in conjunction with FIG. 1 to FIG. 8B below.

Referring now to the drawings, and more particularly to FIG. 1 through FIG. 8B, where similar reference characters denote corresponding features consistently throughout the figures, there are shown preferred embodiments and these embodiments are described in the context of the following exemplary system and/or method.

FIG. 1 is an illustrative system (alternatively referred as human parameter monitoring system) to monitor human health, in accordance with some embodiments of the present disclosure. In an embodiment, the human parameter monitoring system 100 includes processor(s) 104, communication interface(s), alternatively referred as or input/output (I/O) interface(s) 106, and one or more data storage devices or memory 102 operatively coupled to the processor(s) 104. The system 100, with the processor(s) is configured to execute functions of one or more functional blocks of the system 100.

Referring to the components of the system 100, in an embodiment, the processor(s) 104 can be one or more hardware processors 104. In an embodiment, the one or more hardware processors 104 can be implemented as one or more microprocessors, microcomputers, microcontrollers, digital signal processors, central processing units, state machines, logic circuitries, and/or any devices that manipulate signals based on operational instructions. Among other capabilities, the processor(s) 104 is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud, and the like.

The I/O interface(s) 106 can include a variety of software and hardware interfaces, for example, a web interface, a graphical subject interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface(s) 106 can include one or more ports for connecting a number of devices (nodes) of the system 100 to one another or to another server.

The memory 102 may include any computer-readable medium known in the art including, for example, volatile memory, such as static random-access memory (SRAM) and dynamic random-access memory (DRAM), and/or non-volatile memory, such as read only memory (ROM), erasable programmable ROM, flash memories, hard disks, optical disks, and magnetic tapes.

Figure 2A:
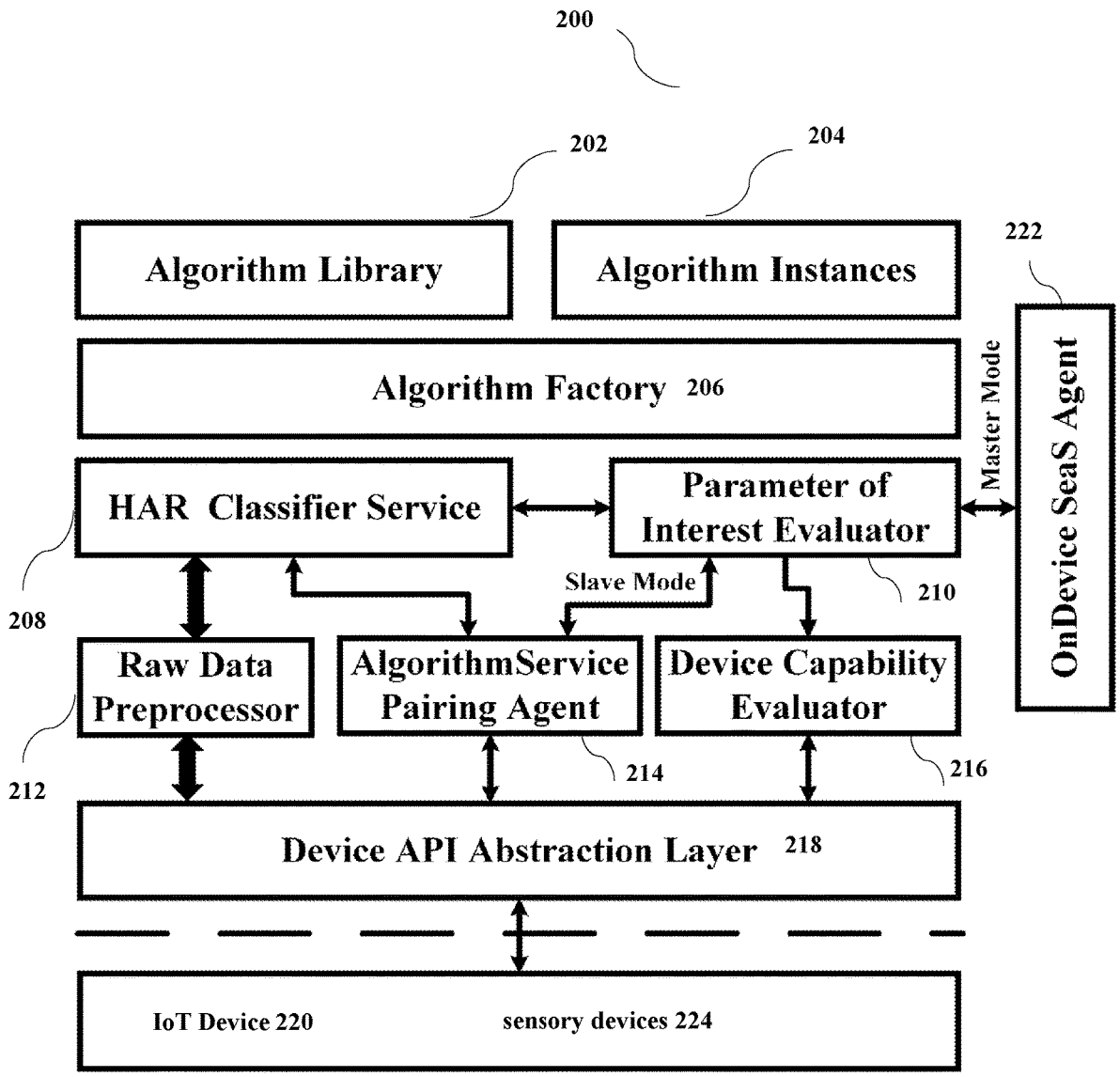
FIG. 2A illustrates a functional on-device algorithm service components of an exemplary hardware implementation of the system of FIG. 1 for executing algorithms corresponding to human parameters in accordance with some embodiments of the present disclosure.
Figure 2B:
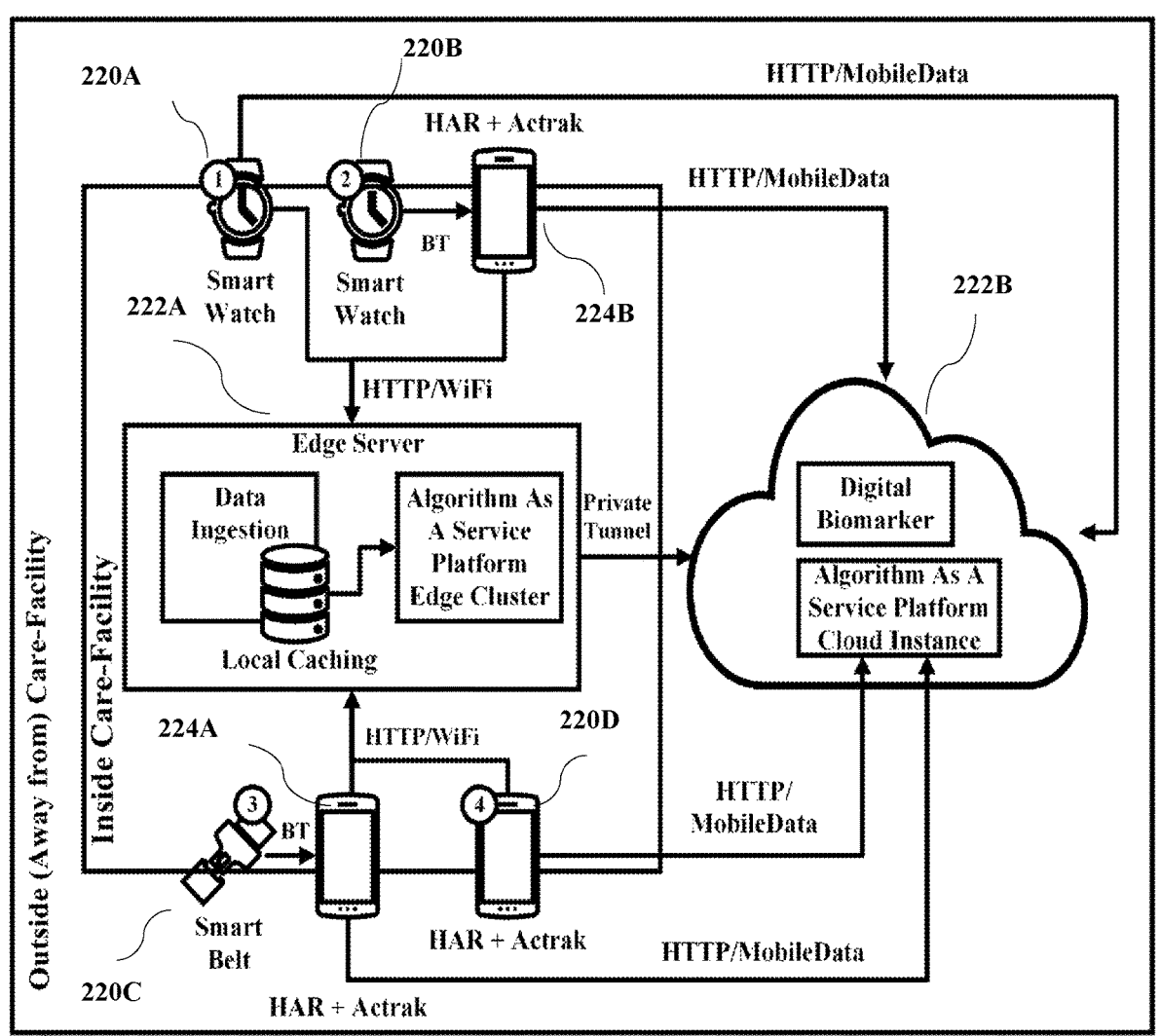
FIG. 2B illustrates a block diagram of an exemplary hardware implementation of the system of FIG. 1 for monitoring human parameters, in accordance with some embodiments of the present disclosure.

In an embodiment, the memory 102 includes a plurality of modules 108 can also include various sub-modules as depicted in FIG. 2A and FIG. 2B, such as an edger server 302, a cloud server 304, a plurality of sensory devices 306A, 306B, . . . 306N, and a plurality of IoT devices 308A, 308B, . . . 308N. The plurality of modules 108 include programs or coded instructions that supplement applications or functions performed by the system 100 for executing different steps involved in the process of monitoring daily living activities of human in a monitoring environment of the system 100. The plurality of modules 108, amongst other things, can include routines, programs, objects, components, and data structures, which performs particular tasks or implement particular abstract data types. The plurality of modules 108 may also be used as, signal processor(s), node machine(s), logic circuitries, and/or any other device or component that manipulates signals based on operational instructions. Further, the plurality of modules 108 can be used by hardware, by computer-readable instructions executed by the one or more hardware processors 104, or by a combination thereof.

The memory 102 may comprise information pertaining to input(s)/output(s) of each step performed by the processor(s) 104 of the system 100 and methods of the present disclosure. Functions of the components of system 100, for identifying malicious agent while handling subject request having at least one sensitive attribute, are explained in conjunction with FIG. 2 and FIG. 3 providing flow diagram, architectural overviews, and performance analysis of the system 100.

FIG. 2A illustrates a functional on-device algorithm service components of an exemplary hardware implementation of the system of FIG. 1 for executing algorithms corresponding to human parameters in accordance with some embodiments of the present disclosure. The on-device algorithm service components includes an algorithm library 202, an algorithm instances 204, an algorithm factory pattern 206, an HAR classifier service 208, a parameter of interest evaluator 210, a raw data processor 212, an algorithm service pairing agent 214, a device capability evaluator 216, a device API abstraction layer 218, an IoT device OS 220 and sensory device API layer 222, and an on-device SeaS agent 222 224.

The algorithm library 202 of the system 200 provides static or dynamic components for example jar files in case of Android, static objects (SO) in Linux, and the like.

The algorithm instances 204 of the system 200 run time instances are generated by the algorithm factory pattern.

The algorithm factory pattern 206 of the system 200 implements factory pattern for instantiating appropriate algorithms.

The human activity recognition (HAR) classifier service 208 of the system 200 can be viewed as a node or a chain of nodes forming a branch of hierarchical class tree structure or a complete hierarchical structure. Each algorithm is designed to generate events which are used to trigger subsequent algorithms and thus these events form a branch or link between the tree nodes.

The parameter of interest evaluator 210 queries the on-device SeaS agent 222 for at least one health parameter of interest to be monitored. The cloud server may be the SeaS agent.

The raw data processor 212 of the system 200 is responsible for converting the continuous time series data into overlapping windows of 'x' seconds each. Further this component extracts various features from each time window.

The algorithm service pairing agent 214 pairs the devices available with the subject.

The device capability evaluator 216 of the system 200 provides capabilities of the devices available with the subject.

The device API abstraction layer 218 of the system 200 provides APIs to access the continuous sensory data captured by the sensors.

The IoT device OS 220 of the system 200 and sensory device API layer 222 of the system 200 stores information related to each IoT device and each sensory device present with the subject.

The on-device SeaS agent 222 of the system 200 prompts the subject to log out from previous smartphone device and sign in from new smartphone device.

The device operating system and its application programming interface layer. For example: android, android wear and thereof.

The abstraction layer 218 of the system 200 provides platform agnostic uniform interface. This layer uses platform specific API adaptors.

The algorithm service pairing agent 214 of the system 200 implements signaling protocol for communication with other paired devices running a version of human parameter monitoring system. The algorithm service pairing agent 214 of the system 200 may not be limited to but operates on top of Bluetooth or Wi-Fi.

FIG. 2B illustrates a block diagram of an exemplary hardware implementation of the system of FIG. 1 for monitoring human parameters, in accordance with some embodiments of the present disclosure. The system 200 may be an example of the system 100 (FIG. 1). In an example embodiment, the system 200 may be embodied in, or is in direct communication with the system, for example the system 100 (FIG. 1). In an embodiment, the system 200 may be alternatively referred as a data privacy risk monitoring system.

The edge server 222A of the system 200 computes time-sensitive data on the plurality of IoT devices and is utilized in remote locations where there is limited or no connectivity to the cloud server 222B. For example, in geriatric care, patient care, old age home and the like facilities where hundreds of devices are co-located with the edge server.

The cloud server 222B of the system 200 comprise a digital biomarker which utilizes algorithm as a service platform cloud instance. The cloud server stores the data provided by the plurality of sensory devices and the plurality of IoT devices.

The plurality of sensory devices 220A, 220B, . . . 220N may include a smart belt, smartwatch, sleep monitoring device, motion device and the like. It is noted that the plurality of sensory devices may have capability to connect with the cloud server or may connect with the cloud sever via the plurality of IoT devices. The edge server 222A manages data processing on the plurality of sensory devices for efficiently identifying and report activities of daily living performed by the subject.

The plurality of IoT devices 224A, 224B, . . . 224N may include at least one IoT device capable of connecting with the cloud server 222B.

Example scenarios where a subject requests the system to monitor a plurality of human parameters for a pre-defined time interval or for an interval of time. The plurality of human parameters may include calorie count, heartbeat rate, GAIT analysis, posture monitoring, sleep analysis and the like or the example scenarios as mentioned below.

Example 1 Activity tracking using standalone wrist wearable device or a smartwatch.

Example 2 Activity tracking using only smartphone.

Example 3 Activity tracking using the wrist wearable device along with the smartphone and other sensory devices.

Scenario 1 of Example 3 When smartwatch is slave and smartphone is the master device.

Scenario 2 of Example 3 When both the smartwatch and the smartphone tries to be the master device.

Scenario 3 of Example 3 When at least one smartphone and one sensory device tries to connect.

Given the plurality of IoT devices and the plurality of sensory devices only a subset k of n is used in actual deployment. The plurality of sensor configurations are provided for deployment of a hierarchical classifier model that optimizes number of human activities detected and determines where to compute the subset k configurations.

Forming a hierarchy of on-device hierarchical sensing pipeline helps to selectively activate corresponding hierarchical on-device sensing pipelines. Therefore, algorithm execution is restricted to the selected active hierarchical pipeline. This reduces computing requirements, and all data processing takes place on edge devices. Implementing other activity detection systems periodically sends raw data from the sensors to the cloud server or to the local server. However, the system sends the data for each subject and store it in a database where memory consumption is high. The present system sends a file containing the final output for example in JSON format or in a protobuf and the like to the server by subject. This optimizes for the size of data transferred and stored in the database and reduces computing load on cloud where CPU usage is reduced considerably.

The example scenarios may be performed using at least one of the IoT device, or the sensory device, or the combination of both. Each type of sensory device produces different type of raw data and might require appropriate preprocessing pipelines depending on at least one of the example. Some scenarios require sensors of at least one sensory device to be "always-on" where data is preferred to be processed in the edge server 222B to reduce cost incurred on account of data transfer, storage, and cloud resources.

The on-device hierarchical sensing pipeline optimizes cost and memory based on daily activities of human parameter to be monitored on the master device.

However, for subjects whose physical sensors are always on, and where one of the plurality of sensory devices cannot access the data on the nearby edge server 222A is transmitted over the internet to the cloud server 222B. It is also possible to use the plurality of sensory devices for human activity tracking. The plurality of sensory devices can use the same sensors or overlapping sensor sets or different sensors corresponding to the activity. For example, mobile phones and smartwatches may have accelerometers and gyroscopes. Therefore, for detecting hand gestures such as drinking, smoking, and waving, this method chooses data from the smartwatch rather than the mobile device due to efficiency. In such scenario, the sensory device positioned on the human body plays important role in activity detection. Therefore, the system needs logical capabilities to make such decision based on the sensor positioned on the.

Figure 3:
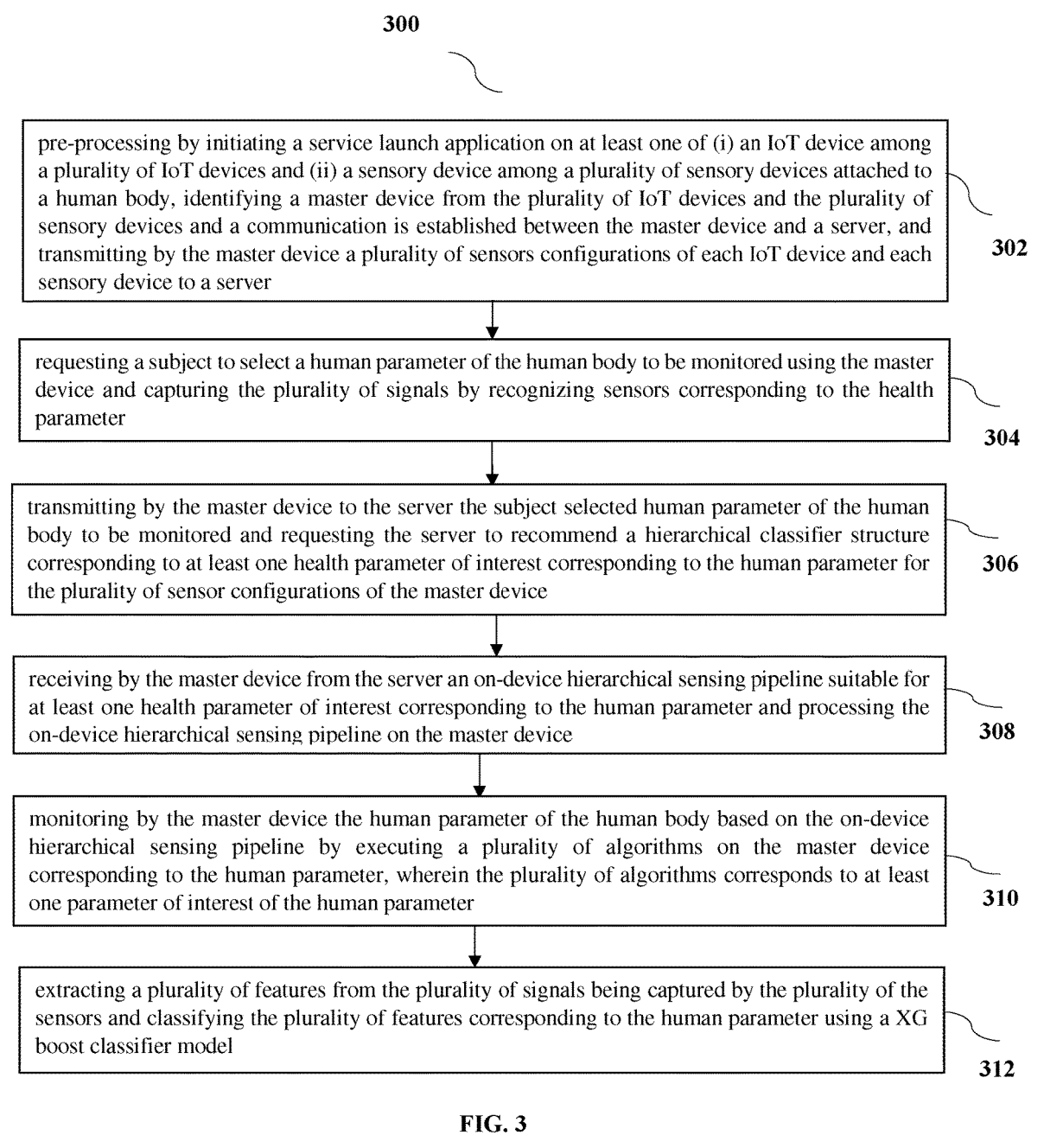

FIG. 3 is a flowchart of an exemplary method of operation for monitoring human parameters using the system of FIG. 1, in accordance with some embodiments of the present disclosure. In an embodiment, the system 100 comprises one or more data storage devices or the memory 102 operatively coupled to the processor(s) 104 and is configured to store instructions for execution of steps of a method 300 by the processor(s) or one or more hardware processors 104. The steps of the method 300 of the present disclosure will now be explained with reference to the components or blocks of the system 100 as depicted in FIG. 1 through FIG. 2, and the steps of flow diagram as depicted in FIG. 3 through FIG. 8B. Although process steps, method steps, techniques or the like may be described in a sequential order, such processes, methods, and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

At step 302 of the method 300 the one or more hardware processors 104 performs pre-processing by initiating a service launch application on at least one of an IoT device among a plurality of IoT devices and a sensory device among a plurality of sensory devices attached to a human body. Each of the sensory device and each of the IoT device captures a plurality of signals via a plurality of sensors. Further, the method identifies a master device from the plurality of IoT devices and the plurality of sensory devices and a communication is established between the master device and a server. The master device further transmits a plurality of sensors configurations of each IoT device and each sensory device to a server.

The service launch application or may be alternatively referred as on-device SeaS agent 222 executes as background service running on at least one of the IoT device or the sensory device. The service launch application is responsible for registering the available plurality of IoT devices and the plurality of sensory devices currently available on the on-device SeaS agent 222. This on-device SeaS agent 222 also exposes APIs for updating device capabilities, querying parameters of interest and updating parameter data.

The master device transmits a plurality of sensors configurations of each IoT device and each sensory device to the server. Here, the master device is being identified from among at least one of the IoT device and the sensory device. The server includes the edge server 222A and the cloud server 222B.

The master device is identified based on the IoT device or the sensory device capabilities.

Figure 4:
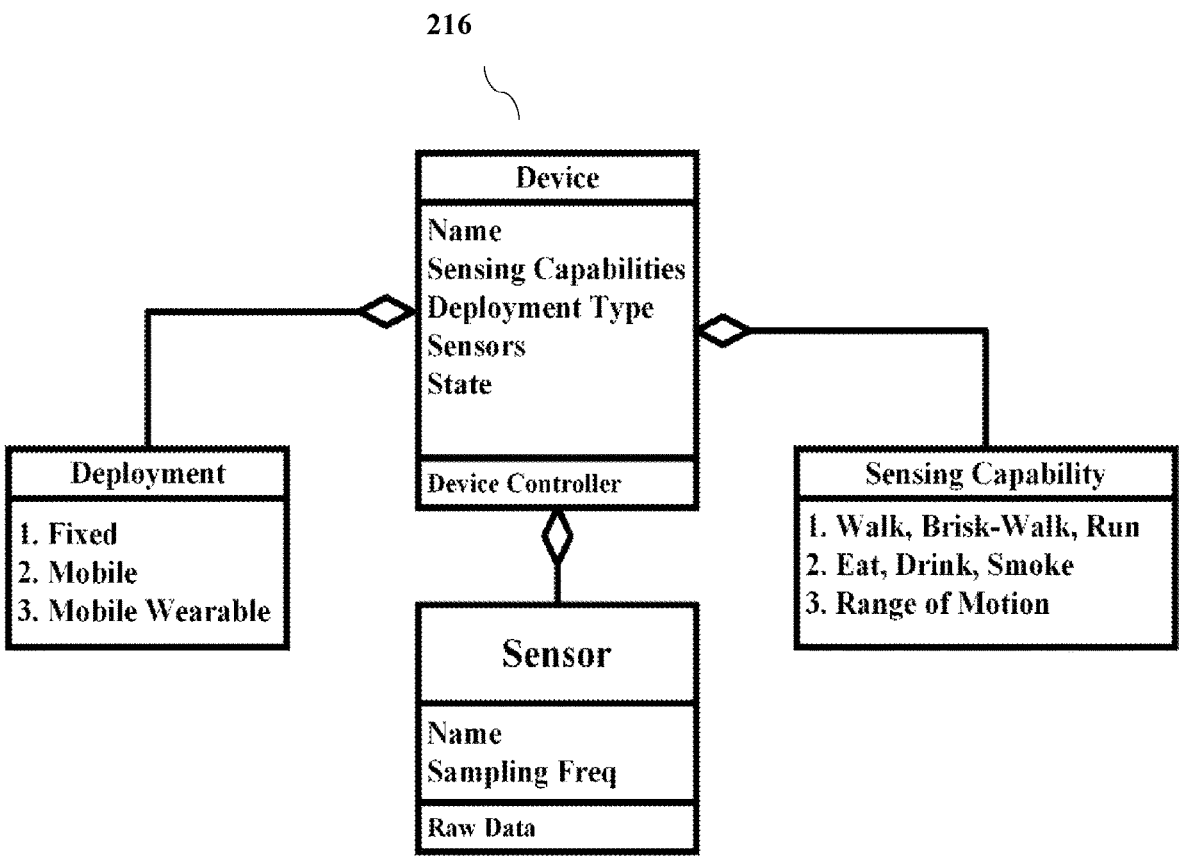
FIG. 4 illustrates an example IoT device capability having a plurality of sensors to monitor human activities using the system of FIG. 1, in accordance with some embodiments of the present disclosure.

Referring now FIG. 4 illustrating an example IoT device capability having a plurality of sensors to monitor human activities using the system of FIG. 1. The FIG. 4 depicts each IoT device or the sensory device type having sensor corresponding to activities to be monitored. The device capability evaluator 216 is responsible for device identification and extracting information about on-device sensors. The framework views the device as a composite or aggregate collection of sensors and algorithms that adds to the sensing capability of corresponding device. For example, the plurality of sensors may include an accelerometer and gyroscope generating tri-axial data, which are processed and analyzed by algorithms to translate into activities.

At step 304 of the method 300 the one or more hardware processors 104 request a subject to select a human parameter of the human body to be monitored using the master device and capturing the plurality of signals by recognizing sensors corresponding to the human parameter. The master device transmits the plurality of signals corresponding to the health parameter of the human body to the server. The server may be the cloud server and an edge server being the device itself.

Referring to the above Example 1 Activity tracking using standalone wrist wearable device or the smartwatch.

When the smartwatch is the only active sensory device. The system gets activated when the smartwatch is powered ON or booted. The smartwatch on-device application on The smartwatch on-device application uses the sensor manager or equivalent to search for the plurality of sensory devices available on the smartwatch. Further, a plurality of sensors available on the device gets registered. In this scenario, the on-device application determines the host device type as the smartwatch. Since the host device is the smartwatch its role is not the master device by default. To confirm its role, it checks if the host is paired with the smartphone being the master device. Therefore, the smartwatch can be used in this scenario, so the host cannot be paired. If the host device has networking capability, then the host on-device application will act as the master device. If the host does not have networking capability the smartwatch uses local buffering and sends the data to smartphone when connected.

Example 2 Activity tracking using only smartphone. When the smartphone is the only active sensory device. The system gets activated when the smartphone is turned ON. The on-device application on the smartphone looks up for the available sensors on the device using the sensor manager or its equivalent. It then registers the list of sensors available on the smartphone. The on-device application then determines the host's device type, the smartphone in this scenario. Since the host device is the smartphone its role by default is master device.

Example 3 Activity tracking using the wrist wearable device along with the smartphone.
In this scenario two devices such as the smartwatch and the smartphone is available with the subject. The on-device application on the smartwatch and the smartphone search for the plurality of sensors available, registers the plurality of sensors and further determines the device host type, the smartwatch, and the smartphone.

Scenario 1 of Example 3-When the smartwatch being one among the sensory device is slave then the smartphone is the master device. The smartphone by default acts as the master device and the paired device (one among the sensory device) acts as the slave where the smartwatch is the sensory device in this scenario.

Scenario 2 of Example 3-When the smartwatch and the smartphone tries to be the master device and if the smartwatch and the smartphone are not paired, then, both the devices act as the master devices. Then, the cloud server receives information from both the master devices acting as the real master device.

At step 306 of the method 300 the one or more hardware processors 104 transmit by the master device to the server the subject selected health parameter of the human body to be monitored and requesting the server to recommend a hierarchical classifier structure corresponding to at least one health parameter of interest corresponding to the human parameter for the plurality of sensor configurations of the master device.

Here, at least one health parameter of interest may be calorie count, GAIT information, sleep analysis. Further, while the master device is operating in MASTER mode, the master device queries using the APIs provided by the on-device SeaS agent 222 for at least one health parameter of interest. Whereas when all other IoT devices and the sensory devices operates in the SLAVE mode the health parameter is queried from the algorithm service pairing agent 214.

At step 308 of the method 300 the one or more hardware processors 104 receive by the master device from the server an on-device hierarchical sensing pipeline suitable for at least one health parameter of interest and processing the on-device hierarchical sensing pipeline on the master device.

The master device executes the hierarchical sensing pipeline on the master device or on a combination of the master device and a slave device, wherein the slave device being at least one of the sensory devices.

Figure 5:
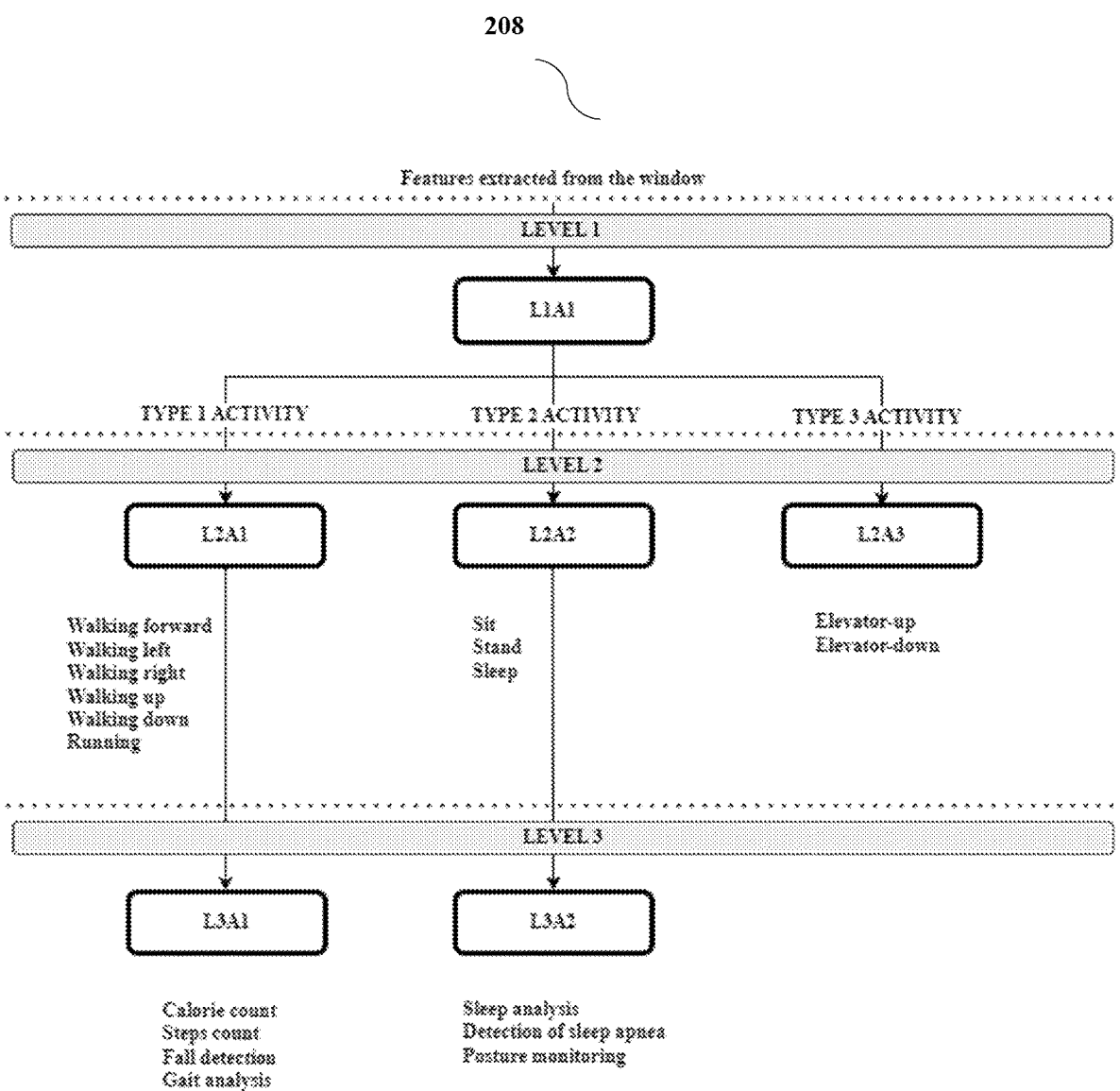
FIG. 5 illustrates an on-device hierarchical sensing pipeline to be executed by the master device using the system of FIG. 1, in accordance with some embodiments of the present disclosure.

Referring now FIG. 5 illustrating the on-device hierarchical sensing pipeline to be executed on the master device using the system of FIG. 1 shows that the on-device hierarchical sensing pipeline is a classic use of the chain of responsibility design pattern, running from the root node to the branches. The holistic tree is the classic strategic design pattern. The number of activities classified according to the ADL is large, and smaller taxonomies are more efficient. It is therefore logical to introduce the hierarchical taxonomy in the sense of "breadth first". The method of the present disclosure HAR (Hierarchical Human Activity Recognition) models and generating dynamic processing pipelines provides an efficient method. In this hierarchical design, each device internal algorithm from among the plurality of algorithms can be viewed as a node in a tree structure forming a multi-level hierarchy. Each of the algorithm is designed to generate events that are used to trigger subsequent algorithms. These events therefore form branches or connections between the tree nodes.

The master device executes the plurality of algorithms suitable for the plurality of sensors on at least one of the sensory device for the subject selected human parameter of the human body.

Each node in the hierarchical classifier structure corresponds to one algorithm among a plurality of algorithms to be executed in the master and in the sensory device.

Referring now to FIG. 5, the LEVEL 1 of design, the activities are categorized into three types based on the displacement of the subject with respect to its position when performing the activity. Based on the input features, the classifier algorithm-1 classifies the human performing activities into at least one of a TYPE 1 or TYPE 2 or TYPE 3 activities. Similarly, based on the output of LEVEL 1, the algorithm is dynamically selected from the plurality of algorithms available at LEVEL 2. Activities are further classified in detail in LEVEL 2 by the selected algorithm. Furthermore, depending on the example scenarios LEVEL 3 selects appropriate algorithms. The smartphone uses the on-device algorithm service as the standalone software component that is being executed in the background. This component has the responsibility of constructing the algorithm processing tree based on the device and scenario configurations and finally managing the lifecycle of each algorithm at runtime. Thus, it is observed that different subjects would subscribe to different algorithms or combinations of algorithms to predict suitable health parameters. Given this scenario, extracting corresponding TYPE sensory data for the subjects is practical. This can be very well achieved using the present disclosure hierarchical sensing pipeline. Thus, saving valuable resources.

At step 310 of the method 300 the one or more hardware processors 104 monitor by the master device the human parameter of the human body based on the on-device hierarchical sensing pipeline by executing a plurality of algorithms on the master device corresponding to the human parameter, wherein the plurality of algorithms corresponds to at least one parameter of interest of the human parameter.

The HAR classifier service 208 will instantiate appropriate algorithms using the algorithm factory pattern 206 for the corresponding edge server 222A. This service will be responsible for passing the events to the next levels to the appropriate algorithms. In cases where the next levels are implemented over a different edge server 222A the events will be communicated via the algorithm service pairing agent 214.

At step 312 of the method 300 the one or more hardware processors 204 extract a plurality of features from the plurality of signals being captured by the plurality of the sensors and classifying the plurality of features corresponding to the human parameter using a XG boost classifier model.

To evaluate the present method the human activity (USC-HAD) dataset was utilized and sampled at continuous time series data in samples of about three seconds each with a 50% overlap. However, if any human activity demands dynamic windowing the same could be achieved in subsequent levels of the Hierarchical framework.

Feature extraction—The plurality of features are divided into four parts comprising a time domain features, a frequency domain features, a discrete wavelet transform (DWT) based features, and an entropy-based features. The time domain features are the correlation between acceleration and angular velocity, a vector magnitude, mean of the acceleration sample (X and Z axes), and variance of the angular velocity sample (X and Z axes). The frequency domain features include $Y_{(t,s)}$ which is calculated considering all the harmonics available in the sample of three seconds along the axis of gravity axis (X-axis), p1 and $P_{1TP}$, where the area under the power spectrum at a dominant frequency and its ratio to the total area under the power spectrum. The features such as standard deviation and root mean square (RMS) values are extracted from aD2, aD3, dA3, and dD3 coefficients as the DWT-based features. Entropy-related features include permutation entropy, spectral entropy, approximate entropy, and singular-value decomposition entropy.

Classifier Design—The classifier design includes the classifiers in the LEVEL 1 and the LEVEL 2 of the "L2A1 classifier" that deals with classifying activities that involve the subject movement from one place to another. The "L2A2 classifier" further classifies the stationary activities. The "L2A3" involves activities that neither belong to TYPE 1 nor TYPE 2 when the subject is standing stationary inside an elevator. Samples classified as TYPE 3 activities follow a dynamic sliding window until the end of activity is detected.

Figure 6A:
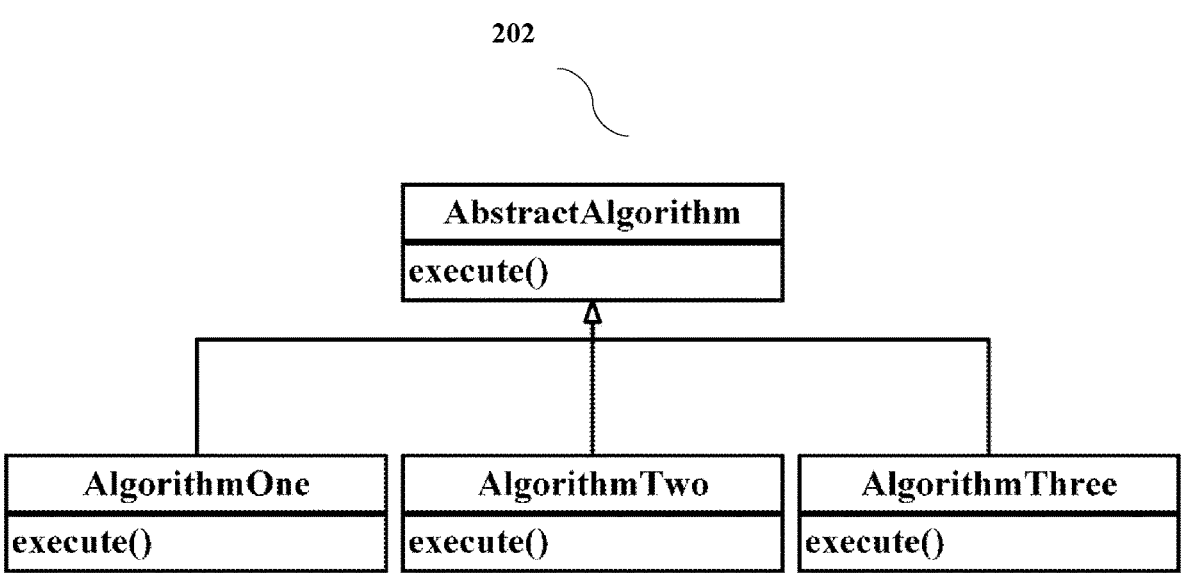
FIG. 6A illustrates an abstract algorithm class structure exemplary hardware implementation using the system of FIG. 1 executed on the master device in accordance with some embodiments of the present disclosure.
Figure 6B:
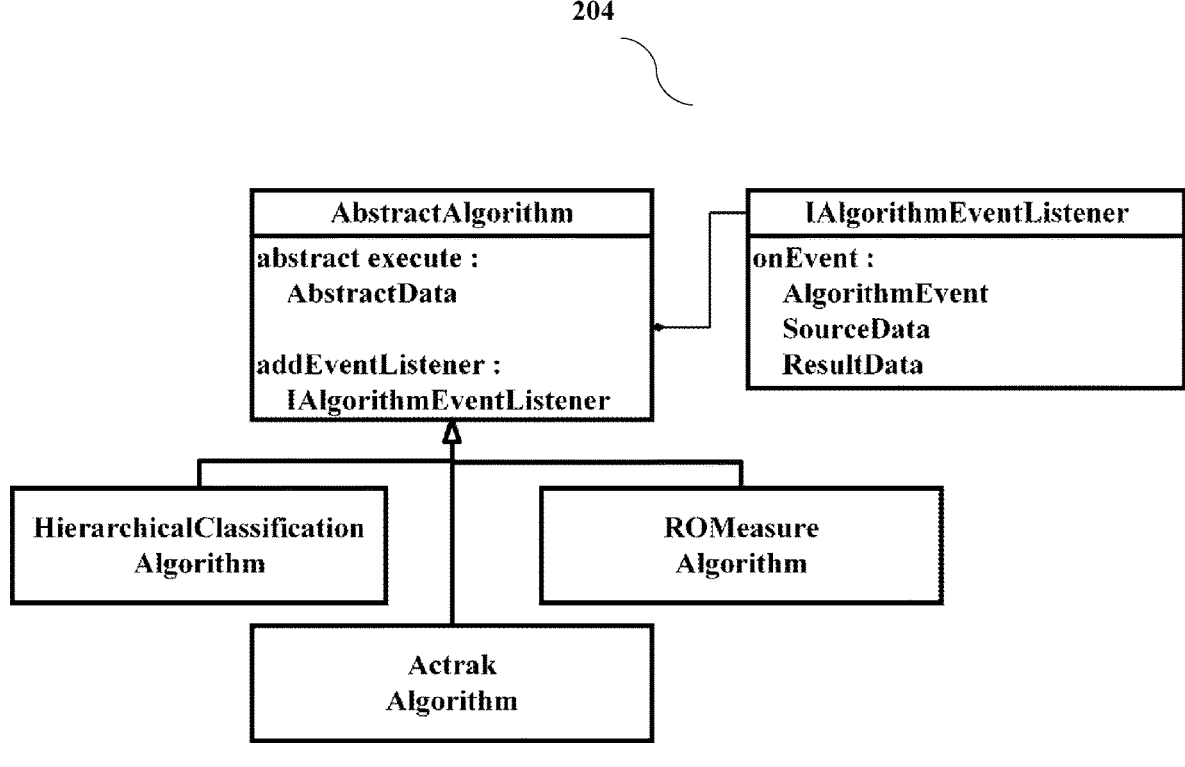
FIG. 6B illustrates an abstract algorithm class sensing pipeline exemplary hardware implementation using the system of FIG. 1 executed on the master device in accordance with some embodiments of the present disclosure.

FIG. 6B illustrates an abstract algorithm class structure exemplary hardware implementation using the system of FIG. 1 executed on the master device in accordance with some embodiments of the present disclosure.

Figure 6C:
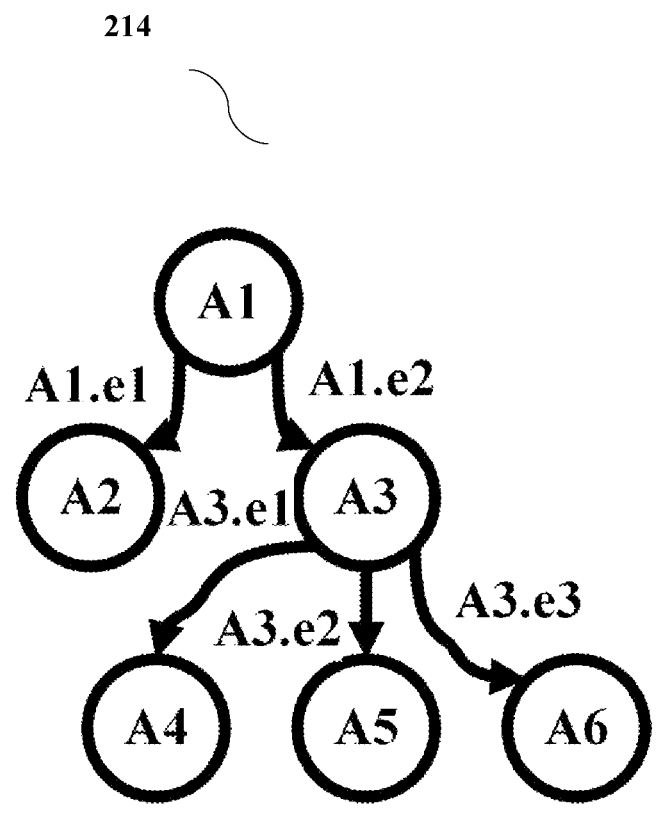
FIG. 6C illustrates an algorithm class on-device sensing pipeline using the system of FIG. 1, in accordance with some embodiments of the present disclosure.

FIG. 6C illustrates an abstract algorithm class sensing pipeline exemplary hardware implementation using the system of FIG. 1 executed on the master device in accordance with some embodiments of the present disclosure.

FIG. 6D illustrates an algorithm class on-device sensing pipeline using the system of FIG. 1, in accordance with some embodiments of the present disclosure. The algorithm service is a standalone software component which executes in the background. This component has the responsibility of constructing the algorithm processing tree based on the master device and corresponding scenario configurations, and manages the life cycle of each algorithm at runtime.

Figure 7B:
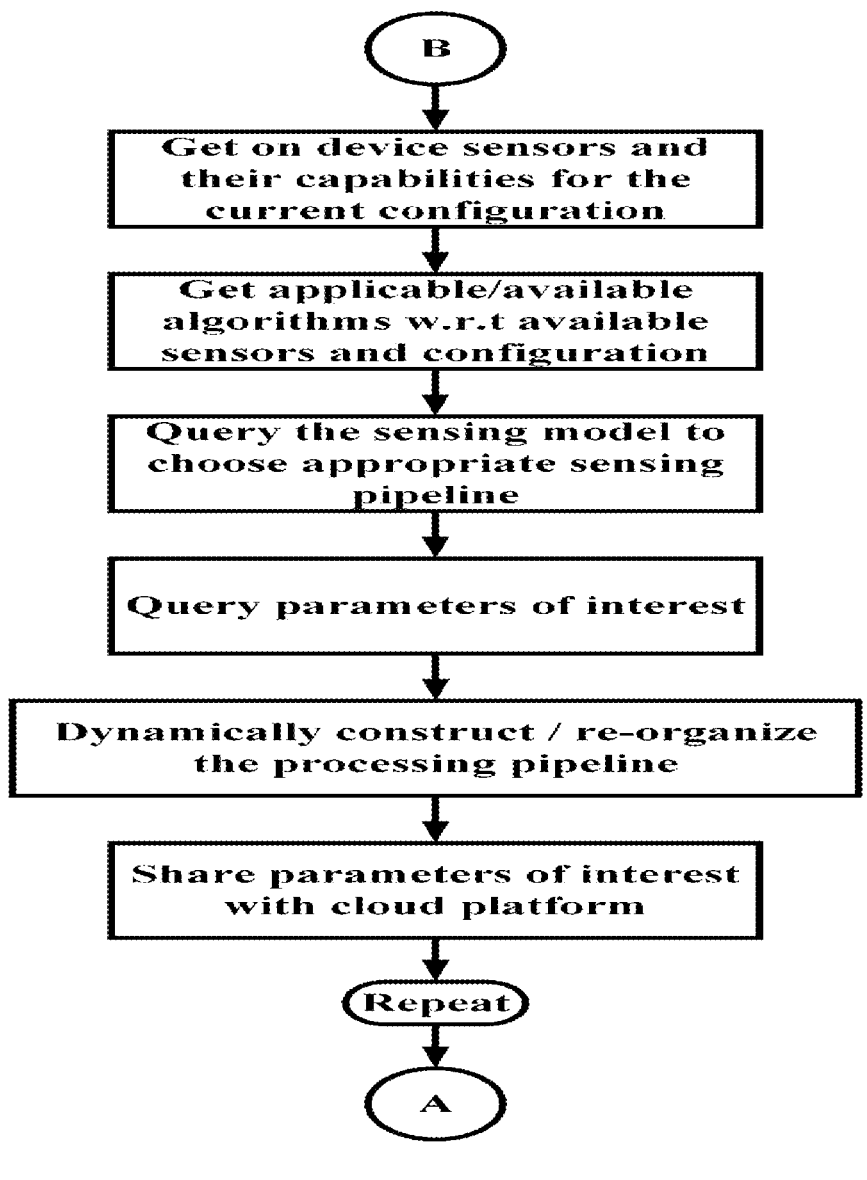

FIG. 7A and FIG. 7B illustrates an example method of operation for monitoring human parameters using the system of FIG. 1 corresponding to the plurality of sensors in accordance with some embodiments of the present disclosure.

Referring now again to the above Example 1 Activity tracking using standalone wrist wearable device or a smartwatch.

Assuming 'P' be the subject enrolled for elderly care facilities. 'P' has been enrolled to elderly care premises for 'T' number of days. The network is set up once the smartwatch is switched ON. The smartwatch initiates the service launch application software 'On-device Algorithm Service'. The algorithm service pairing agent 214 identifies the software detects list of devices paired with the smartwatch. The on-device SeaS agent 222 detects the device type of the edge client it is hosted on the smartwatch in this scenario using the device capability evaluator 216. Since the device type of the edge client it is hosted on is not the smartphone, the service launch application software further checks if the device is connected with the smartphone. Here, the subject 'P' selects only the smartwatch the service launch application software does not find any smartphone connected. The service launch application software checks if the smartwatch has networking capabilities. If 'YES', the smartwatch acts as the master device in this scenario. If 'NO' the smartwatch uses local buffering and dumps the data to the master device smartphone when connected. The master device smartwatch establishes connection with the edge-server or the cloud server utilizing the APIs provided by the on-device SeaS agent 222. The master device captures the sensory configuration, compute availability of all the devices using the device capability evaluator). This data is relayed to the server. The server responds with a list of health-related parameters which could be derived given the input data received from the plurality of available sensors corresponding to the health parameter. The master device is responsible for communicating the selected choice of health-related parameters to the cloud using on-device SeaS agent 222 APIs. Based on the choice of the health-related parameters, the sensory configuration and compute availability the server designs a Hierarchical processing pipeline for the master to implement.

Data Capture—The device API abstraction layer 218 provides APIs to access the continuous sensory data captured by the plurality of sensors. Using the raw data pre-processor 212 the software derives features required for the selected processing pipeline of algorithms.

Data processing—The hierarchical sensing pipeline received by the master device is then implemented using the HAR classifier service 208. HAR classifier service 208 is responsible for execution of the hierarchical processing pipeline provided by the server. HAR classifier service 208 relays instructions related to the algorithm libraries 202 and parts of algorithm processing pipeline to be implemented on to the other paired devices via the algorithm service pairing agent 214. The service uses the algorithms provided by the algorithm library 202. It further instantiates runtime instances using the algorithm factory pattern 206. The algorithm instances 204 are cascaded as required by the processing pipeline to derive the required health parameters.

Referring now to the above described Example 2—Activity tracking using only smartphone.

Once the smartphone is switched ON, The smartphone initiates the application software 'On-device Algorithm Service'. Using the algorithm service pairing agent 214 the software detects list of devices paired with the smartphone. The software detects the device type of the edge-client it is hosted on the smartphone in this case using the device capability evaluator 216. Since the device type of the edge client, it is hosted on is the smartphone, the software sets the device as the master device for the scenario. Since in this scenario the subject 'P' selects only the smartphone the software does not find any other devices connected. The master device smartphone establishes connection with the edge server 222A or the cloud server 222B utilizing the APIs provided by the on-device SeaS agent 222. The master device captures the plurality of sensory configurations and compute availability of the devices, if any using the device capability evaluator. This data is relayed to the server. The server responds with at least one of the human parameter which could be derived from the input data received from the plurality of available sensors. The master device is responsible for communicating the selected choice of health-related parameters to the cloud using on-device SeaS agent 222 APIs. Based on the choice of the health related parameter corresponding the plurality of sensory configuration are used compute availability the server designs the hierarchical sensing pipeline for the master device to implement.

Referring now to the Example 3—Activity tracking using the smartphone and other sensory devices.

Scenario 1 of Example 3—When the smartwatch is slave, and the smartphone is the master device. Here, when all the devices are paired with each other network is setup once all the devices are switched ON. Here, all the devices initiate the application software 'On-device Algorithm Service'. Using the algorithm service pairing agent 214, the software detects list of devices paired with the host device. The software detects the device-type of the edge-client it is hosted on using the device capability evaluator. The smartphone in the paired network by default upgrades to be the master device. The master device smartphone establishes connection with the edge-server or the cloud-server utilizing the APIs provided by the on-device SeaS agent 222. The master device captures the sensory configuration, compute availability of all the paired devices using the device capability evaluator 216 and the algorithm service pairing agent 214. This data is relayed to the server. The server responds with a list of health-related parameters which could be derived given the input data (received from the list of available sensors). The master device is responsible for communicating the selected choice of health-related parameters to the cloud using on-device SeaS agent 222 APIs.

Data capture—The device API abstraction layer 218 of the sensory devices provides APIs to access the continuous sensory data captured by the sensors. Using the raw data preprocessor 212 the software derives features required for the selected processing pipeline of algorithms.

Data processing—The Hierarchical processing pipeline received by the master device is then implemented using the HAR classifier service 208. HAR classifier service 208 is responsible for execution of the hierarchical processing pipeline provided by the server. HAR classifier service 208 relays instructions related to the algorithm libraries and parts of algorithm processing pipeline to be implemented on to the other paired devices via the algorithm service pairing agent, the paired one/multiple slave devices activate their HAR classifier service to execute the assigned respective parts of algorithm processing pipeline. Once the execution is completed the outputs are relayed to the next component in the pipeline. The service uses the algorithms provided by the algorithm library 202. It further instantiates runtime instances using the algorithm factory pattern 204. The algorithm instances 204 cascaded as required by the processing pipeline to derive the required human parameter.

Scenario 2 of Example 3 When both the smartwatch and the smartphone tries to be the master device.
All the devices initiate the application software 'On-device Algorithm Service'. Using the Algorithm service pairing agent, the software detects list of devices paired with the host device (none in this scenario). The software detects the device-type of the edge-client it is hosted on using the device capability evaluator 216. All the devices with networking capabilities upgrade to become the master device. All the master device establish connection with the edge-server or the cloud-server utilizing the APIs provided by the on-device SeaS agent 222. The server detects multiple master for the same subject. The master device captures the sensory configuration, compute availability of all the paired devices (no paired devices in this scenario). This data is relayed to the server. The server responds with a list of health-related parameters which could be derived given the input data (received from the plurality of available sensors).

Data capture—The device API abstraction layer 218 of each sensory device provides APIs to access the continuous sensory data captured by the sensors. Using the raw data preprocessor 212 the software derives features required for the selected processing pipeline of algorithms on all devices.

Data processing—The server detects multiple edge-client master devices with overlapping sensory capabilities located at different areas on the subject, each one having varying degrees of efficacy to derive a particular intermediate step result/final health parameter partially or fully. The server selects which health parameters could be efficiently derived by which of the edge-client masters. The server dynamically distributes different processing pipelines amongst edge devices depending on their efficacy and efficiency. The Hierarchical processing pipeline received by each master device is then implemented using the HAR classifier service 208. HAR classifier service 208 is responsible for execution of the Hierarchical processing pipeline provided by the server. HAR classifier service 208 relays instructions related to the algorithm libraries 202 and parts of algorithm processing pipeline to be implemented on to the other paired devices via the algorithm service pairing agent 214. The service uses the algorithms provided by the algorithm library 202. It further instantiates runtime instances using the algorithm factory component 206. The algorithm instances 204 are cascaded as required by the processing pipeline to derive the required health parameters. Finally, the server receives different health parameters from different edge-devices which are consolidated.

Scenario 3 of Example 3 when at least one smartphone and one sensory device tries to connect.

The network setup, all the devices initiate the application software 'On-device Algorithm Service'. Using the algorithm service pairing agent 214, the software detects list of devices paired with the host device. The software detects the device-type of the edge-client it is hosted on using the device capability evaluator 216. The on-device SeaS agent 222 shall prompt the subject to log out from previous smartphone device and sign in from new smartphone device. After 'T' number of days, subject 'P' returns home. The selected master device now directly communicates with the cloud server in the absence of any of the edge server.

Figure 8A:
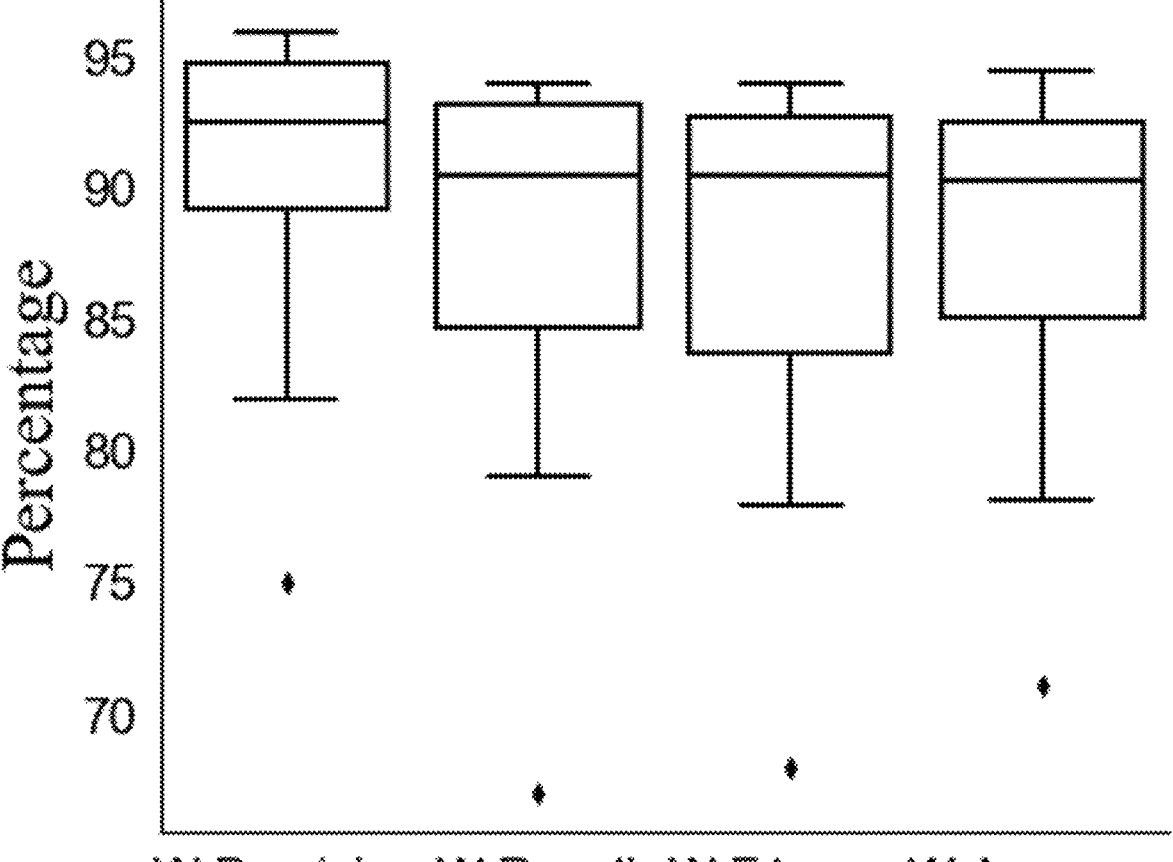
FIG. 8A illustrates a graphical representation of LOSOCV weighted performances of activities across all the subjects using the system of FIG. 1 in accordance with some embodiments of the present disclosure.

FIG. 8A illustrates a graphical representation of LOSOCV weighted performances of activities across all the subjects using the system of FIG. 1 in accordance with some embodiments of the present disclosure.

Results—10-fold cross-validation results: 10-fold cross-validation results using different classifiers on the USC-HAD data show that the best combination for the classification approach is to take a combination of three XGBoost classifiers. Table I shows a detailed classification report concerning the activities for 10-fold cross-validation. The result shows that the performance of the algorithm deteriorates for the Type 3 activities, while for the others, the F1-score is consistently more than 0.96. The main reason for under-performance in the case of Type III activities can be attributed to the uneven distribution of type III activities which is just 0.88% of the total number of samples.

TABLE I

| Classification report on the activities for 10-fold cross-validation | | | | |
|---|---|---|---|---|
| | Precision | Recall | F1-score | support |
| Walking forward | 0.97 | 0.98 | 0.97 | 490 |
| Walking left | 0.97 | 0.98 | 0.97 | 327 |
| Walking right | 0.96 | 0.98 | 0.97 | 349 |
| Walking upstairs | 0.97 | 0.95 | 0.96 | 264 |
| Walking downstairs | 0.97 | 0.95 | 0.96 | 245 |
| Running forward | 1.00 | 1.00 | 1.00 | 216 |
| Jumping up | 1.00 | 0.98 | 0.99 | 124 |
| Sitting | 1.00 | 0.98 | 0.99 | 330 |
| Standing | 0.97 | 1.00 | 0.99 | 296 |
| Sleeping | 1.00 | 0.98 | 0.99 | 481 |
| Elevator-up | 0.92 | 0.86 | 0.89 | 14 |
| Elevator-down | 0.92 | 0.86 | 0.89 | 14 |
| Macro avg | 0.97 | 0.96 | 0.97 | 3150 |
| Weighted avg | 0.98 | 0.98 | 0.98 | 3150 |

Leave One Subject Out Cross Validation: Models are often tested on the same subject data as used to train the model, which is not the scenario in the real world. To assess the performance of the model on different subjects unknown to the train data performing LOSOCV. Each box and whisker represents the spread of the corresponding metric for every subject in the data set. It is observed that the minimum for all subjects lies well above the 70% value and the Inter Quartile Range lies above the 80% mark for all metrics. Also, the median values for all metrics lie above 90%. With an average weighted precision of 90.71% and weighted accuracy of 87.79% the approach works consistently well.

FIG. 8B illustrates a graphical representation of comparison of existing techniques with the present disclosure using the system of FIG. 1 in accordance with some embodiments of the present disclosure. Comparison with previous works: The frameworks results with three recent previous works as can be seen achieving an accuracy of 97.96% when tested on the USC HAD dataset. In comparison, the DCNN method in achieves an accuracy of 97.01%, achieves an accuracy of 97.80%. Both of these works use deep learning techniques. This achieves an accuracy of 92.43% and precision of 92.50%.

In one embodiment, the formation of hierarchical structure on-device-sensing pipeline helps to selectively activate corresponding hierarchical pipeline. Thus, algorithm execution is limited to selected active hierarchical pipeline. Thus, reducing the computer requirement. The entire data processing is attempted to be executed on the edge device. Any other system meant for recognizing activities when implemented, regularly transmits raw sensor data (to cloud server or the local server). Referring to the USC HAD dataset, a file containing one minute of data has an average size of 720 kbs. With this detail, the system would need to transmit and save to database, 720×60 kbs/hour, per subject. Hence 720×60×24 kbs/day=1,036,800 kbs/day (1.0368 GB/day from single edge device containing two sensors for single subject). The present disclosure reduces this to a single file to the server consisting of final output in the JSON format, this results in optimization corresponding to the size of data transferred and stored in database and consequent reduction of server CPU usage.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein addresses unresolved problem of monitoring human parameters activities of daily living (ADLs). The embodiment thus provides method and system for monitoring human parameters using hierarchical human activity sensing. Moreover, the method of the present disclosure processes continuous mobility data from the plurality of sensors on the client edge-device by optimizing the on-device sensing pipelines. This reduces cost of data transfer and CPU usage and also provides data accuracy and flexibility.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means, and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method for monitoring activities of daily living, the method further comprising:
    pre-processing via one or more hardware processor by,
    initiating a service launch application on at least one of (i) an IoT device among a plurality of IoT devices and (ii) a sensory device among a plurality of sensory devices attached to a human body, wherein each of the sensory device and each of the IoT device captures a plurality of signals via a plurality of sensors,
    identifying a master device from the plurality of IoT devices and the plurality of sensory devices, wherein communication is established between the master device and a server and wherein the master device transmits the plurality of signals corresponding to a health parameter of the human body to the server using APIs provided by the on-device SeaS (Sensing as a service) agent, and transmitting by the master device a plurality of sensors configurations of each IoT device and each sensory device to a server;

requesting a subject via the one or more hardware processors to select a human parameter of the human body to be monitored using the master device and capturing the plurality of signals by recognizing sensors corresponding to the health parameter, wherein the master device transmits the plurality of signals corresponding to the health parameter of the human body to the server;

transmitting by the master device via the one or more hardware processors to the server the subject selected human parameter of the human body to be monitored and requesting the server to recommend a hierarchical classifier structure corresponding to at least one health parameter of interest corresponding to the human parameter for the plurality of sensor configurations of the master device;

receiving by the master device from the server via the one or more hardware processors an on-device hierarchical sensing pipeline suitable for at least one health parameter of interest corresponding to the human parameter and processing the on-device hierarchical sensing pipeline on the master device; and monitoring by the master device via the one or more hardware processors the human parameter of the human body based on the on-device hierarchical sensing pipeline by executing a plurality of algorithms on the master device corresponding to the human parameter, wherein the plurality of algorithms corresponds to at least one parameter of interest of the human parameter.

2. The processor implemented method of claim 1, further comprising extracting a plurality of features from the plurality of signals captured by the plurality of the sensors and classifying the plurality of features corresponding to the human parameter using a XG boost classifier model.

3. The processor implemented method of claim 1, wherein the server includes one of an edge serve and a cloud server.

4. The processor implemented method of claim 1, wherein the master device is identified based on the IoT device or the sensory device capabilities.

5. The processor implemented method of claim 1, wherein the master device executes the hierarchical sensing pipeline on the master device or on a combination of the master device and a slave device, wherein the slave device being at least one of the sensory devices.

6. The processor implemented method of claim 1, wherein the master device executes the plurality of algorithms suitable for the plurality of sensors on at least one of the sensory device for the subject selected human parameter of the human body.

7. The processor implemented method of claim 1, wherein the on-device hierarchical sensing pipeline optimizes cost and memory based on daily activities of human parameter to be monitored on the master device.

8. The processor implemented method of claim 1, wherein the service launch application triggers at least one IoT device or at least one sensory device to check capability to connect to the server via internet.

9. The processor implemented method of claim 1, wherein each node in the hierarchical classifier structure corresponds to one algorithm among the plurality of algorithms to be executed in the master and in the sensory device.

10. The processor implemented method of claim 1, wherein the subject may monitor the human parameter of the human body by using at least one of the IoT device, the sensory device, and the combination of the IoT device and the sensory device.

11. A system for monitoring activities of daily living comprising:

a memory storing instructions;

one or more communication interfaces; and one or more hardware processors coupled to the memory via the one or more communication interfaces, wherein the one or more hardware processors are configured by the instructions to:

pre-process by, initiating a service launch application on at least one of an IoT device among a plurality of IoT devices and a sensory device among a plurality of sensory devices attached to a human body, wherein each of the sensory device and each of the IoT device captures a plurality of signals via a plurality of sensors, identifying a master device from the plurality of IoT devices and the plurality of sensory devices, wherein a communication is established between the master device and a server and wherein the master device transmits the plurality of signals corresponding to a health parameter of the human body to the server using APIs provided by the on-device SeaS (Sensing as a service) agent, and transmitting by the master device a plurality of sensors configurations of each IoT device and each sensory device to a server;

request a subject to select a human parameter of the human body to be monitored using the master device and capturing the plurality of signals by recognizing sensors corresponding to the health parameter, wherein the master device transmits the plurality of signals corresponding to the health parameter of the human body to the server;

transmit via the master device to the server the subject selected human parameter of the human body to be monitored and requesting the server to recommend a hierarchical classifier structure corresponding to at least one health parameter of interest corresponding to the human parameter for the plurality of sensor configurations of the master device;

receive via the master device from the server an on-device hierarchical sensing pipeline suitable for at least one health parameter of interest corresponding to the human parameter and processing the on-device hierarchical sensing pipeline on the master device; and monitor via the master device the human parameter of the human body based on the on-device hierarchical sensing pipeline by executing a plurality of algorithms on the master device corresponding to the human parameter, wherein the plurality of algorithms corresponds to at least one parameter of interest of the human parameter.

12. The system of claim 11, wherein the one or more hardware processors are further configured to extract a plurality of features from the plurality of signals captured by the plurality of the sensors and classifying the plurality of features corresponding to the human parameter using a XG boost classifier model.

13. The system of claim 11, wherein the server includes an edge server and a cloud server.

14. The system of claim 11, wherein the master device is identified based on the IoT device or the sensory device capabilities.

15. The system of claim 11, wherein the master device executes the hierarchical sensing pipeline on the master device or on a combination of the master device and a slave device, wherein the slave device being at least one of the sensory devices, and wherein the master device executes the plurality of algorithms suitable for the plurality of sensors on at least one of the sensory device for the subject selected human parameter of the human body.

16. The system of claim 11, wherein the on-device hierarchical sensing pipeline optimizes cost and memory based on daily activities of human parameter to be monitored on the master device.

17. The system of claim 11, wherein the service launch application triggers at least one IoT device or at least one sensory device to check capability to connect to the server via internet.

18. The system of claim 11, wherein each node in the hierarchical classifier structure corresponds to one algorithm among the plurality of algorithms to be executed in the master device and in the sensory device.

19. The system of claim 11, wherein the subject may monitor the human parameter of the human body by using at least one of the IoT device, the sensory device, and the combination of the IoT device and the sensory device.

20. One or more non-transitory machine-readable information storage mediums comprising one or more instructions which when executed by one or more hardware processors cause:

pre-processing via one or more hardware processor by, initiating a service launch application on at least one of (i) an IoT device among a plurality of IoT devices and (ii) a sensory device among a plurality of sensory devices attached to a human body, wherein each of the sensory device and each of the IoT device captures a plurality of signals via a plurality of sensors, identifying a master device from the plurality of IoT devices and the plurality of sensory devices, wherein communication is established between the master device and a server and wherein the master device transmits the plurality of signals corresponding to a health parameter of the human body to the server using APIs provided by the on-device SeaS (Sensing as a service) agent, and transmitting by the master device a plurality of sensors configurations of each IoT device and each sensory device to a server;

requesting a subject via the one or more hardware processors to select a human parameter of the human body to be monitored using the master device and capturing the plurality of signals by recognizing sensors corresponding to the health parameter, wherein the master device transmits the plurality of signals corresponding to the health parameter of the human body to the server;

transmitting by the master device via the one or more hardware processors to the server the subject selected human parameter of the human body to be monitored and requesting the server to recommend a hierarchical classifier structure corresponding to at least one health parameter of interest corresponding to the human parameter for the plurality of sensor configurations of the master device;

receiving by the master device from the server via the one or more hardware processors an on-device hierarchical sensing pipeline suitable for at least one health parameter of interest corresponding to the human parameter and processing the on-device hierarchical sensing pipeline on the master device; and monitoring by the master device via the one or more hardware processors the human parameter of the human body based on the on-device hierarchical sensing pipeline by executing a plurality of algorithms on the master device corresponding to the human parameter, wherein the plurality of algorithms corresponds to at least one parameter of interest of the human parameter.

* * * * *